United States Patent [19]
Marttila

[11] Patent Number: 5,685,844
[45] Date of Patent: Nov. 11, 1997

[54] MEDICINAL FLUID PUMP HAVING MULTIPLE STORED PROTOCOLS

[75] Inventor: Constance M. Marttila, Fallbrook, Calif.

[73] Assignee: Abbott Laboratories, Abbott Park, Ill.

[21] Appl. No.: 369,732

[22] Filed: Jan. 6, 1995

[51] Int. Cl.[6] ................................................... A61M 1/00
[52] U.S. Cl. ................................................................ 604/65
[58] Field of Search .................................. 604/65–67, 30, 604/31, 32–34, 246, 249; 128/DIG. 12, DIG. 13

[56] References Cited

U.S. PATENT DOCUMENTS

| | | | |
|---|---|---|---|
| 4,676,776 | 6/1987 | Howson | 604/31 |
| 4,810,243 | 3/1989 | Howson | 604/31 |
| 4,828,545 | 5/1989 | Epstein et al. | 604/66 |
| 4,850,972 | 7/1989 | Schulman et al. | 604/151 |
| 4,854,324 | 8/1989 | Hirschman et al. | 128/655 |
| 4,865,584 | 9/1989 | Epstein et al. | 604/67 |
| 4,898,578 | 2/1990 | Rubalcaba, Jr. | 604/66 |
| 5,041,086 | 8/1991 | Koenig et al. | 604/65 |
| 5,088,981 | 2/1992 | Howson et al. | 604/31 |
| 5,100,380 | 3/1992 | Epstein et al. | 604/67 |
| 5,153,927 | 10/1992 | Coutré et al. | 364/413.02 |
| 5,256,157 | 10/1993 | Samiotes et al. | 604/246 |
| 5,298,021 | 3/1994 | Sherer | 604/66 |
| 5,304,126 | 4/1994 | Epstein et al. | 604/67 |

FOREIGN PATENT DOCUMENTS

| | | |
|---|---|---|
| 0503670 | 9/1992 | European Pat. Off. . |
| WO 93/21978 | 11/1993 | WIPO . |
| WO-A-9408647 | 4/1994 | WIPO . |

OTHER PUBLICATIONS

Medfusion Model 2010, Operations Manual, Medfusion Inc Revision 1, Jun. 1991.
IMED Gemini PC-4 Volumetric Pump/Controller Operator's Manual, Feb. 15, 1993.
"Today's Anaesthetist," Advance in Patient Controlled Analgesia Management, vol. 9, No. 6, Nov./Dec. 1994, 2pp.

*Primary Examiner*—Manuel Mendez
*Attorney, Agent, or Firm*—Neal D. Marcus

[57] ABSTRACT

A pump (23) used to infuse a fluid into a patient (27) is controlled in accordance with a plurality of parameters entered by an operator. These parameters define a protocol that is applied in controlling the operation of the pump to determine the rate, volume, and timing of the fluid infusion. The operator enters the parameters using a keypad (16) in response to prompts provided on a display (18). Once the parameters for a current protocol are entered, they can be stored as a speed protocol by selecting that option from a menu appearing on the display. Up to three speed protocols can be stored in memory in the disclosed preferred embodiment. When preparing to infuse a medicinal fluid, an operator can elect to enter a new protocol or to select an appropriate speed protocol stored in memory for loading as the current protocol. Use of stored speed protocols saves time and reduces the likelihood of errors that can occur when data defining the parameters controlling the infusion process are entered by an operator.

22 Claims, 8 Drawing Sheets

MEDICINAL FLUID PUMP HAVING MULTIPLE STORED PROTOCOLS

FIELD OF THE INVENTION

The present invention generally pertains to a pump for infusing medicinal liquids into a patient, and more specifically, to a pump that is controlled in accordance with a plurality of parameters that are entered by an operator.

BACKGROUND OF THE INVENTION

Cassette, peristaltic, and other types of motor or solenoid driven pumps are widely employed to infuse medicinal fluids into the cardiovascular systems of patients. These pumps often include a controller that determines the rate at which the medication is infused, the volume or dosage of medicinal fluid administered, whether it is delivered as a bolus or continuous infusion, the time that the administration occurs, and/or the interval of time that the pump will operate. These parameters and others are usually entered into an electronic memory for the pump controller via a user interface control panel on the pump by medical personnel, based upon the type and concentration of the drug being administered, and patient specific data, such as the patient's weight, age, gender, and medical condition. Although entry of the parameters that control the pump's operation may be relatively straightforward, several minutes may be required to specify all of the data required to define a drug delivery protocol. More importantly, each time that a pump is programmed to administer a specific medicinal fluid, there is a risk that human error may cause improper values for the parameters to be entered.

To avoid the potential risks involved in programming a pump each time it is used to deliver a different type of medication, it is not uncommon for hospitals and other medical facilities to purchase and employ multiple pumps, with each pump programmed to administer a particular type of drug in a defined manner. Any programming required to tailor the administration of a drug to a patient is thereby minimized by using a separate pump for each type of drug and delivery protocol commonly required. Thus, one pump will be used to administer a certain pain management drug, and a different pump will be programmed to continuously administer a saline/glucose fluid. The only changes required for a use of a pump with each patient receiving the same type of medicinal fluid may be the entry of one or more patient dependent parameters, such as the total drug volume to be delivered. Alternatively, if a single pump of the conventional type is used to administer different drugs involving totally different protocols, a medical practitioner trained to program the pump must be available each time that it is used to infuse a different drug. A medical facility must therefore either maintain a pump programmed for each drug typically infused or must ensure that properly trained personnel are always available to reprogram a pump each time that it is used to administer a different drug. However, the latter solution to this problem increases the risk that a life-threatening error might occur when the pump is reprogrammed and requires that properly trained personnel always be available to reprogram the pumps that are used.

Clearly, it would be desirable if a pump could be used to administer different types of medicinal fluids without the need for manual reprogramming each time that the type of medicinal fluid infused is changed. In U.S. Pat. No. 4,676,776, a system is disclosed that includes a delivery unit, which is remotely coupled to a programming unit through a telephone line and modem. Alternatively, the system will accept a programmable logic cartridge that is programmed by the programming unit and hand-carried to the pump. The remote programming unit includes an operationally independent computer that manages the protocols for operating the fluid delivery unit. The computer of the programming unit has access to a number of both predefined and operator programmed protocols that are stored in a database integral within its memory. The delivery unit does not require a microprocessor to define the protocol for delivering a fluid, since all of the operational parameters are set by the remote computer in the programming unit. Each time that the delivery unit is to be used to administer a different drug, the appropriate predefined or operator defined protocol for that drug is downloaded from the remote computer into a control and logic module of the delivery unit. However, only one protocol at a time can be loaded into the delivery unit. Either the telephone/modem interconnection or a programmable logic cartridge suitably programmed for the correct drug must be used to transfer the protocol that will be employed from the remote computer into the delivery unit.

The requirement for transferring the protocol from the remote computer to the delivery unit represents a significant drawback to this prior art infusion system, since it is often not convenient to physically transport a programmable logic cartridge between a remote computer and the delivery unit or to arrange for a modem and telephone line interconnection between the computer in the programming unit and the logic module of the delivery unit. The patent specifically teaches that it is advantageous to employ a remote computer for defining the protocol because microprocessors used to control pumps are subject to possibly undetected failures and have limited processing capability.

Other types of conventional pumps include multiple channels, each channel being capable of infusing a different type of drug into a patient according to a different delivery protocol. However, even these pumps do not enable the operator to select between different previously stored protocols for the administration of a medicinal fluid on a single channel. Accordingly, each time that a channel is used to deliver a different type of drug than that previously administered, the protocol for the new drug must be reentered into the pump for that channel.

None of the prior art pumps for administering drugs via a specific channel allow an operator to store protocols for different drugs integrally within the pump. Integral storage of the different protocols within the pump is important to obviate the need to transfer a selected protocol from a remote computer, and more importantly, to avoid the cost of a separate computer in which such protocols are stored in a database.

SUMMARY OF THE INVENTION

In accordance with the present invention, a pump is defined for administering a fluid to a patient. The pump includes a fluid drive unit that is adapted to couple with a fluid line and to force fluid from a source to the patient through the fluid line. A control is coupled to the fluid drive unit to control its operation. Also provided is a memory in which a plurality of protocols are stored. These protocols each specify at least one parameter that is used to control the fluid drive. A user interface that is integral with the pump and is coupled to the control and to the memory enables the operator to enter at least one parameter for any of the plurality of protocols. With the user interface, one of the protocols can be selected for use by the control in actively controlling the operation of the drive unit so as to administer the fluid to the patient.

Preferably, the parameter entered by the operator includes one of a continuous fluid flow, an intermittent fluid flow, and a bolus fluid flow. It can also include one of a rate of fluid flow, a volume of fluid flow, a time of fluid flow, and a duration of fluid flow. In addition, the parameter may comprise a varying rate of fluid flow.

The user interface enables the operator to define a current protocol and to store the current protocol as one of the plurality of protocols in the memory. The control cooperates with the user interface to enable the operator to review one of the plurality of protocols stored in the memory while the drive unit is being operated in accordance with a different one of the plurality of protocols. Furthermore, the user interface enables the operator to recall one of the plurality of protocols from memory so that it can be employed as a currently active protocol used by the control in controlling the drive unit. In addition, the user interface enables the operator to modify the currently active protocol prior to storing it in the memory. Since the plurality of protocols are integrally stored in memory, a change in the drug that is to be delivered is readily accommodated simply by recalling the protocol from memory that is appropriate for administering the drug. In most cases, there is no need to completely redefine the protocol that must be used each time that the pump is employed to administer a different drug.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
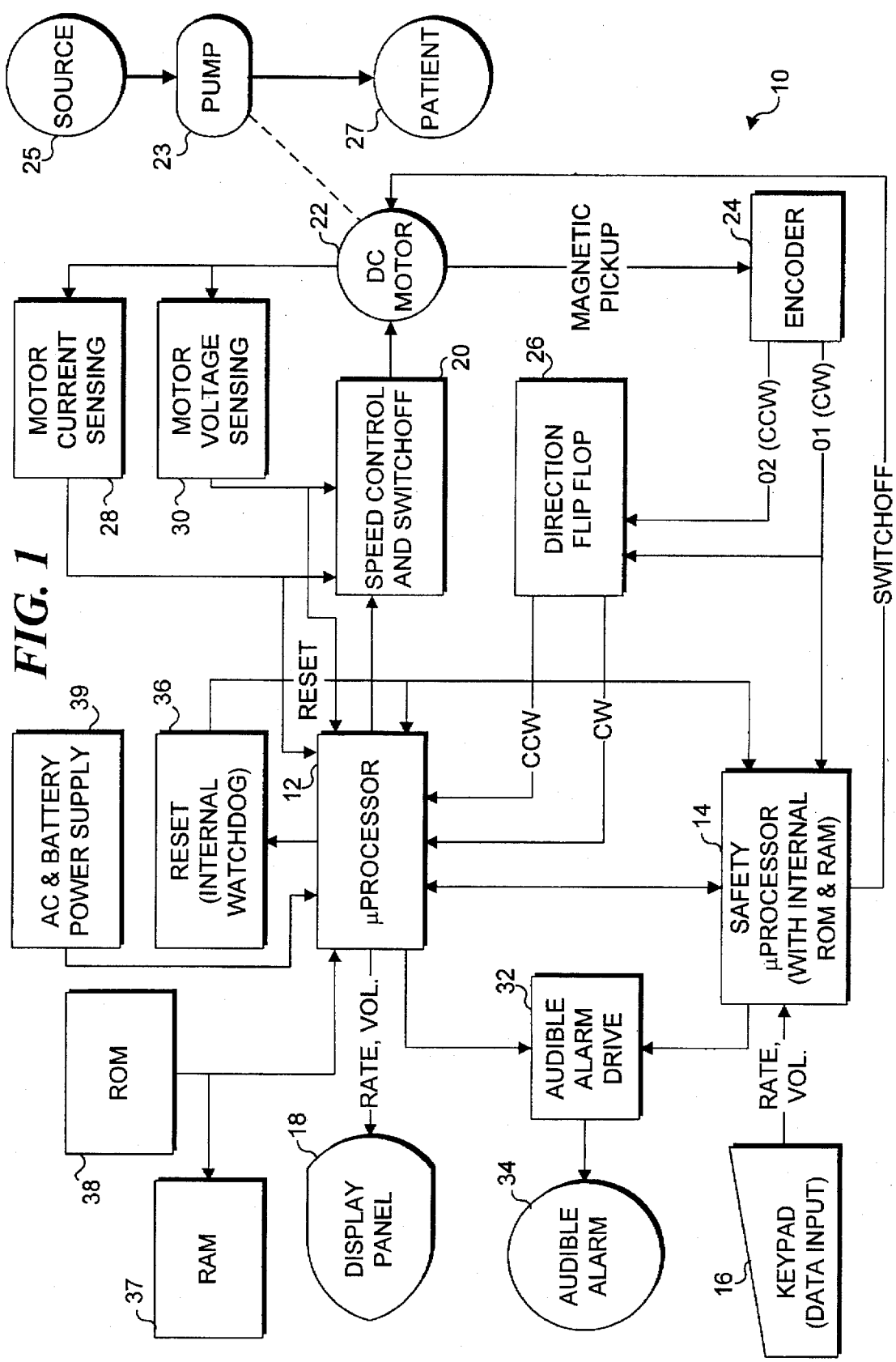
FIG. 1 is a schematic block diagram of a controller for a pump embodying the present invention.

With reference to FIG. 1, a block diagram illustrates the components comprising a control 10 for an integral pump 23 that is used for infusing medicinal fluids from a source 25 into a patient 27 in accordance with the present invention. While the preferred embodiment of this pump forces fluid to flow through a tube set (not shown) using a peristaltic pump 23, it will be apparent from the following description that other types of pumping apparatus (such as a cassette pump) could also implement the present invention, thereby providing the benefits of accessing stored protocols when the pump is used to deliver different drugs or medicinal fluids.

Control 10 includes a microprocessor 12, which implements the primary control functions required to operate pump 23. These functions are defined by a set of program steps that are stored within a read only memory (ROM) 38. The program steps stored in ROM 38 are in the form of a binary code, which is executed by microprocessor 12 to control the operation of various components of the pump following an operator defined protocol. To improve safety and reduce the number of single point failures, a redundant safety microprocessor 14 is included. Safety microprocessor 14 includes internal ROM and random access memory (RAM). In the preferred embodiment, a Motorola Corporation Model MC68L11K1 integrated circuit is used for microprocessor 12, and a Motorola Corporation Type MC68HC705C8 integrated circuit is used for safety microprocessor 14. The preferred embodiment employs an integrated circuit for ROM 38 that has a capacity to store up to 256K bytes of program steps and control data. In addition, an external integrated circuit RAM 37 with a capacity of 32K bytes is coupled to microprocessor 12 to provide storage for data and variables. Data stored within KAM 37 is maintained so long as electrical power is supplied to it. Electrical power is supplied to the pump from either an AC line power supply or a battery pack (conventional or rechargeable), as indicated by AC and battery power supply 39. When both the AC and normal battery power supply is interrupted a backup (lithium) battery (not separately shown) provides power to the control circuitry. Thus, even when pump 23 is not operating, the data stored within the RAM are retained.

Safety microprocessor 14 is responsible for reading data input by an operator on a keypad 16, monitoring motor speed, and providing data access through an RS-232 serial port (not shown). Using the keypad, the operator can specify parameters such as the percentage of volume, the rate, and/or the volume that will be used for administering a particular medicinal fluid. Microprocessor 12 is coupled to safety microprocessor 14 to receive these data for presentation to the operator on a display panel 18, which is directly coupled to microprocessor 12.

Operation of pump 23 is controlled by microprocessor 12 with signals that are input to a speed control and switch off circuit 20. This circuit is connected to a DC motor 22 to control its rate of rotation. Since the preferred embodiment of the present invention pumps fluid using a peristaltic cassette, the rate at which fluid is administered to a patient is directly proportional to the rate at which DC motor 22 rotates. It will thus be apparent that speed control 20 is used for controlling DC motor 22 to achieve the desired rate for infusing fluid into the patient. DC motor 22 includes a Hall effect magnetic pickup (not separately shown) that produces rotational rate signals, which are applied as an input signal to an encoder 24. Encoder 24 processes this input signal, producing a corresponding digital signal "01" indicating the rate of rotation in the clockwise (CW) direction or a corresponding digital signal "02" indicating the rate of rotation in the counterclockwise (CCW) direction. The digital signal corresponding to the rate of rotation in the CW direction is input to both a direction flip flop circuit 26 and to safety microprocessor 14, while the digital signal indicative of the rate of rotation in the CCW direction is input only to direction flip flop 26.

In normal operation, the DC motor and the pump rotate in a CW direction. The DC motor has an attached gearbox (not separately shown), but the encoder indicates shaft revolutions of the DC motor ahead of the gearbox—not at the gearbox output shaft. Slight rotation of the DC motor in the CCW direction can occur due to gearbox "wind-up," especially when the DC motor is turned off and comes to a stop. When the DC motor is again energized, it turns a few degrees before the output shaft actually starts turning. There will thus be "extra" encoder pulses produced that do not accurately account for output gearbox shaft revolutions. On the average, the number of extra CW pulses produced when the DC motor starts will be equal to the number of CCW pulses produced when the DC motor stops. If the number of CCW pulses is subtracted from the total CW pulses, the error in the total CW pulses is corrected, thereby improving flow rate accuracy. This accuracy improvement is significant at low flow rates (less than 1 cc/hr).

Certain fault conditions, such as an empty fluid source container, can cause microprocessor 12 to stop the DC motor. Safety microprocessor 14 can also issue a switch off command to DC motor 22 if it detects that the pump is operating abnormally or requires operator intervention to correct a problem.

To enable control 10 to properly control the rate of rotation of DC motor 22, a motor current sensing circuit 28 provides a current feedback signal to microprocessor 12 and to the speed control. Similarly, a motor voltage sensing circuit 30 provides another feedback signal indicative of the voltage across the windings of the DC motor to microprocessor 12 and to the speed control. These two feedback signals and control signals supplied by microprocessor 12 are employed by speed control and switch off circuit 20 to set and maintain the average rotational speed of DC motor 22 to achieve the desired drug infusion rate.

Either microprocessor 12 or safety microprocessor 14 will respond to conditions requiring operator intervention by activating an audible alarm drive circuit 32. The audible alarm drive circuit produces a drive signal that is applied to an audible alarm 34, causing it to produce a distinctive alarm sound that is used to attract the attention of the operator. Upon hearing the audible alarm sound, the operator knows to check the pump to determine the appropriate corrective action that must be taken. For example, an air-in-line sensor (not shown) monitors the infusion line to detect air bubbles. If air bubbles larger than a predefined size are detected in the infusion line, the air-in-line sensor produces a signal to which microprocessor 12 will respond by stopping the DC motor and activating the audible alarm.

A reset circuit 36 serves as an internal watchdog by checking the software strobing rate on microprocessor 12. If software strobing (a timing signal indicative of the rate at which the microprocessor is executing machine instructions) is not within a predefined range, the reset circuit issues a reset command to both microprocessor 12 and safety microprocessor 14.

Figure 2:
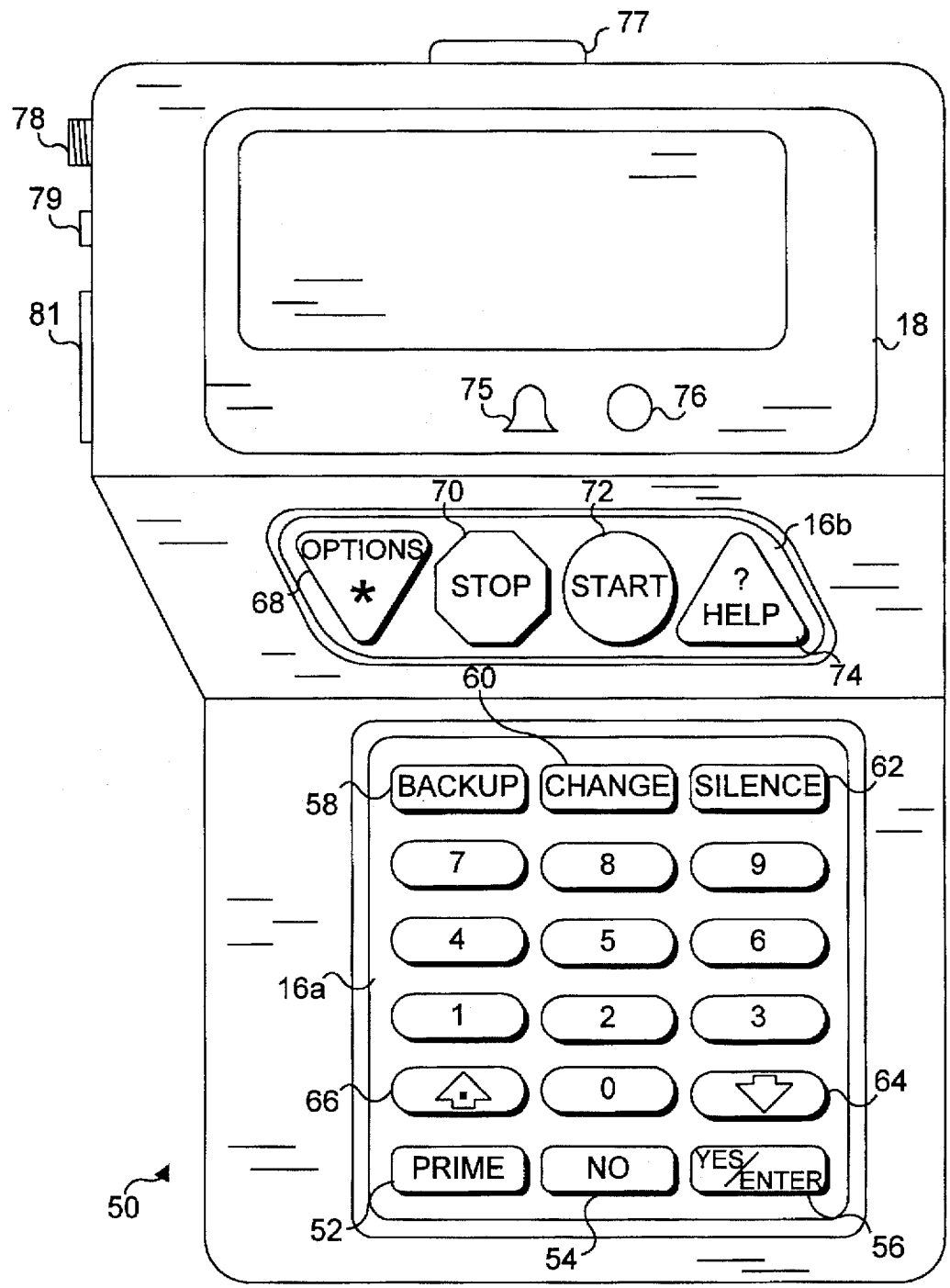
FIG. 2 is a front elevational view of the pump of FIG. 1.

Referring now to FIG. 2, the user interface, which appears on the front of a pump 50, includes a lower keypad section 16a, an upper keypad section 16b, and a display 18, which is disposed above the upper keypad section. Lower keypad section 16a includes 18 keys arranged in an array of three columns and six rows. In addition to the conventional numeric keys 0 through 9, lower keypad 16a includes several special purpose keys. A "PRIME" key 52 is depressed by the operator to manually energize the pump in order to prime and clear air from the infusion line before it is connected to the patient's body. A key 54 labeled "NO" is depressed to enter a negative response to questions that appear on display 18. Conversely, a key 56 labeled "YES/ENTER" is provided to enable the operator to respond in the affirmative to questions appearing on display 18 and to register a numeric entry or to advance to the next display screen when entering data. A key 58 labeled "BACKUP" is used to exit a history or a Help display. In addition, key 58 is used to access previous steps that were entered by the operator when programming the control for a new protocol. Furthermore, the BACKUP key is used for exiting "CHANGE" and "OPTIONS" modes.

A key 60, which is labeled "CHANGE," is used to correct an entry when entering data, for reviewing a program, when changing containers, to enter a new program, and to change a therapy. A "SILENCE" key 62 temporarily silences audible alarm 34 (shown in FIG. 1), enabling the operator to correct the condition that initially caused the alarm without the annoyance of the audible signal continuing.

A combined upwardly pointing arrow and a period appear on a key 66. Similarly, a downwardly pointing arrow appears on a key 64. The up and down arrow keys are used for scrolling through menu selections and through the history of drug infusion that can be selectively provided on display 18. In addition, these two keys are used for scrolling through input selections when entering an infusion protocol. Key 66 is also used for entering a decimal point in numeric data.

In upper keypad 16b, an "OPTIONS" key 68 can be depressed to selectively review a protocol, display, print or clear a drug infusion history for a patient, selectively lock or unlock the keypad, set the air-in-line alarm, set an internal clock used by control 10, access speed protocols, adjust screen contrast and sound level, and to display an alarm log. A hexagonal-shaped key 70, which is labeled "STOP," is provided to enable the operator to selectively stop an infusion at any time. Similarly, a key 72 labeled "START" is provided to enable the operator to start the infusion. As already noted, the operator can access a help screen at any time by depressing key 74.

In the lower portion of display 18 is included a bell-shaped visual signal (light emitting diode (LED))75, which is lighted when an alarm condition occurs. Another visual signal 76 is lighted when the pump is powered using AC line power (instead of the internal power pack batteries).

On the top surface of the pump is disposed a bolus switch 77, which the operator can depress to manually deliver a bolus of the drug currently being infused if the pump is programmed to do so. A jack 79 is provided on the left upper side of the pump to accept a lead from a remote bolus switch (not shown). This remote bolus switch can be activated by the patient when the pump is being used to deliver a pain management drug or for variable time drug infusions (if programmed). Also disposed on the left upper side of the pump is a fitting 78 to which an AC line cord (not shown) can be coupled, and a slide switch 81 that is used for turning the pump off and on.

In the preferred embodiment, the pump can be used for five distinct types of medicinal fluid infusion. Tables 1 through 5 show the various parameters that are entered to define the protocol used to control the pump for each type of infusion. The parameters can selectively be set to read in units of ml, mg, or µg.

TABLE 1

| CONTINUOUS ONLY | |
|---|---|
| PARAMETER | RANGE/COMMENT |
| Rate | 0.1 ml/hr–400 ml/hr |
| Container Size (Total Volume) | 0.1 ml–9999.9 ml |

TABLE 1-continued

CONTINUOUS ONLY

| PARAMETER | RANGE/COMMENT |
| --- | --- |
| Air-in-line Alarm Sensitivity (Hi, Low, Off) | Hi (Bubbles > 75 µl nominal) Low (Bubbles > 250 µl nominal) Off (Bubbles > 2 ml nominal) |

TABLE 2

PARENTERAL NUTRITION

| PARAMETER | RANGE/COMMENT |
| --- | --- |
| Container Size (Total Volume) | 1 ml–9999 ml |
| All Combinations of Taper Up, Taper Down & Continuous | Taper is a gradually increasing or decreasing delivery rate |
| Parenteral Nutrition Volume | 1 ml–9600 ml |
| Total Time for Infusion | 1 min to 24 hr |
| Time Interval for Taper Infusion (If Selected) | 1 min to 3 hr |
| Air-in-line Alarm Sensitivity (Hi, Low, Off) - Optional | Hi (Bubbles > 75 µl nominal) Low (Bubbles > 250 µl nominal) Off (Bubbles > 2 ml nominal) |
| Keep Vein Open (KVO) - Optional | 1 ml/hr–5 ml/hr |

Parenteral Nutrition provides infusion of nutrient fluids that are necessary when a patient is unable to eat food, for example, because of problems with the gastrointestinal system. The rate at which the nutrient solution is infused can be programmed to taper up or down, or to continue on a continuous basis, or any combination of these three variables. The KVO option ensures that sufficient fluid is infused between programmed infusions to prevent blood clots from forming in the vein or in the catheter through which the fluid is infused.

TABLE 3

PAIN MANAGEMENT

| PARAMETER | RANGE/COMMENT |
| --- | --- |
| Select Delivery Mode | Bolus, Continuous, or Combo |
| Container Size (Total Volume) | 0.1 ml–9999.9 ml |
| Rate | 0.1 ml/hr–25.0 ml/hr |
| Size of Bolus (If Bolus Delivery Mode is Used) | Up to 25 ml (5 ml if subcutaneous infusion) - or subject to Limits |
| Bolus Lockout (If Bolus Used) | 5 min–999 min (Time Between Boluses) |
| Infusion Site and Rate Limits at Each | Intravenous or Epidural: 25 ml/hr Subcutaneous: 5 ml/hr |
| Loading Dose (Clinician Administered Bolus) | Not subject to Lockout, but subject to Limits |
| Limit Number of Boluses Administered | For example, 2 boluses/hr |
| Four Hour Volume Limit | Max. total volume in 4 hr period |
| Subcutaneous Limit | 5 ml/hour of Drug Delivery |
| Air-in-line Alarm Sensitivity (Hi, Low, Off) - Optional | Hi (Bubbles > 75 µl nominal) Low (Bubbles > 250 µl nominal) Off (Bubbles > 2 ml nominal) |

Since pain management often enables patient controlled bolus infusion of pain killing drugs, this type of infusion protocol enables the clinician to limit the bolus infusions in several ways. The size of each bolus is defined by the protocol, as are the minimum time between successive boluses and the number of bolus infusions per hour. A further limit is the total volume delivered during a four-hour period. Medical personnel can selectively deliver a bolus infusion or loading dose more frequently than allowed by the bolus lockout time, but are limited by the total volume delivered. The infusion site selected introduces a limit on the volume of the drug delivered to the patient, whether by bolus, continuous, or a combination of bolus and continuous infusion.

TABLE 4

INTERMITTENT

| PARAMETER | RANGE/COMMENT |
| --- | --- |
| Container Size (Total Volume) | 0.1 ml–9999.9 ml |
| Dose Size | 0.1 ml–9600.0 ml |
| Time Interval for Delivery of Dose | 1 min–24 hr |
| Time Interval between Start of Dose Deliveries | Time interval for delivery of dose up to 24 hr |
| KVO (Optional) | 0.1 ml/hr–5 ml/hr |
| Delayed Start Time (Optional) | |
| Air-in-Line Sensitivity (Hi, Low, Off) - Optional | Hi (Bubbles > 75 µl nominal) Low (Bubbles > 250 µl nominal) Off (Bubbles > 2 ml nominal) |

The Intermittent type of infusion is often used to administer antibiotic therapy. Based on the two time intervals and the dose size, the control determines the appropriate rate of delivery.

TABLE 5

VARIABLE

| PARAMETER | RANGE/COMMENT |
| --- | --- |
| Container Size (Total Volume) | 0.1 ml–9999.9 ml |
| Phase Program: Enter Start Time, Stop Time, & Dose | 1–12 Phases Chemotherapy - limited to 24 hr (One Phase Program required) |
| Optional Base Rate: Enter Start Time, Stop Time, & Rate | Rate- 0.1 ml/hr–400 ml/hr |
| Optional Bolus Dose (with Lockout Time) | Up to 25 ml |
| KVO (Optional) | 0.1 ml/hr–5 ml/hr |
| Air-in-line Alarm Sensitivity (Hi, Low, Off) - Optional | Hi (Bubbles > 75 µl nominal) Low (Bubbles > 250 µl nominal) Off (Bubbles > 2 ml nominal) |

The Variable type of infusion, which is typically used to administer chemotherapy, requires that at least one phase program be entered, by selecting the start and stop times, and the dose. In addition, an optional base rate infusion can be added to the protocol by selecting the start time, stop time, and rate.

Figure 3:
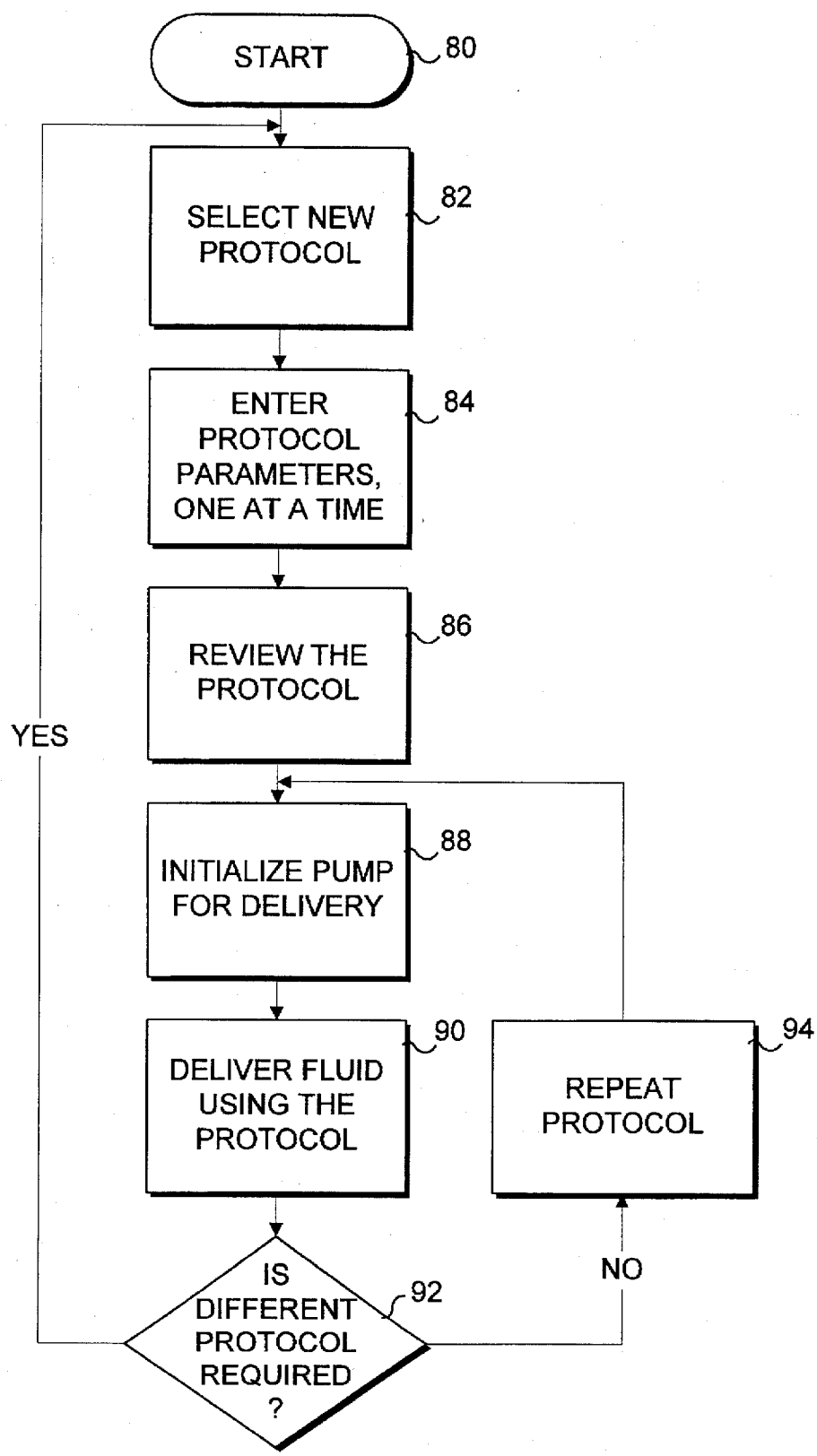
FIG. 3 is a flow chart showing the steps for operating the pump without use of a speed protocol.

In FIG. 3, the steps required to enter parameters for use in controlling the pump to infuse a medicinal fluid are illustrated, beginning at a start block 80. In a block 82, the operator indicates that a new protocol is being selected. Specifically, the operator depresses button 60 and selects "NEW PROGRAM," indicating that the protocol is to be changed. In response, the control for pump 50 prompts the operator to select the type of infusion desired and then prompts the operator to enter each of the protocol parameters for the selected type of infusion, one at a time, as indicated in a block 84. The various parameters that can be controlled by the operator in defining the protocol are noted in the preceding tables and depend upon the type of infusion selected. In addition, the operator can select the units that will be used for the parameters in defining the protocol.

In a block 86, the protocol defined by the operator is shown on display 18 so that the operator can review it.

Assuming that it is correct, in a block 88, the operator initiates the protocol to run by depressing START key 72. As indicated in block 88, this step initializes the pump for delivery of the fluid to be infused from the source container. When the control initializes, it zeroes out any prior values in memory and builds a control table based upon the protocol entered/selected by the operator. In a block 90, the pump delivers the fluid to the patient, in accordance with the parameters comprising the protocol. A decision block 92 determines if a different protocol is required, based upon the operator depressing the CHANGE key and selecting "NEW PROGRAM," or alternatively, selecting "NEW CONTAINER" to repeat the previous protocol, as provided in a block 94.

To repeat the current protocol, the control logic returns to block 88. However, if the operator indicates that a different protocol should be used, the logic proceeds back to block 82. The operator is then requested to indicate which new protocol is to be initiated, leading to the entry of each parameter employed for controlling the pump for that protocol. It should be evident that each time a new protocol is entered in this manner, the operator may inadvertently enter an incorrect parameter, which may result in an error in the delivery of medicinal fluid to the patient. Furthermore, entry of the parameters required to define a protocol each time that a different protocol is required is both inefficient and time consuming. Accordingly, the present invention provides an alternative.

Figure 4:
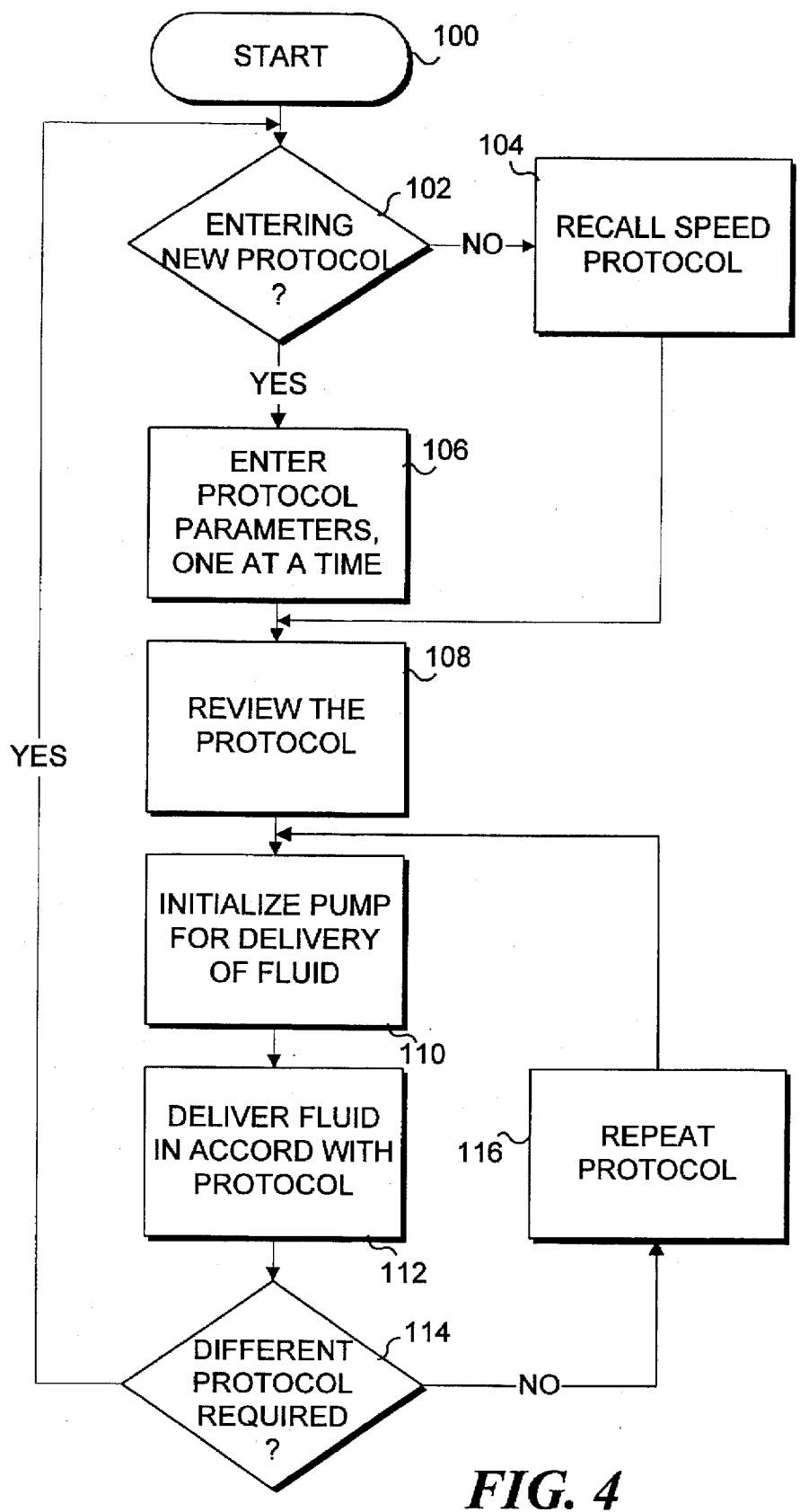
FIG. 4 is a flow chart illustrating the logic involved in operating the pump using speed protocols.

Turning to FIG. 4, control of the pump using a speed protocol that was previously entered is illustrated. The logic begins at a start block 100. Thereafter, in a decision block 102, the operator determines if a new protocol should be entered, i.e., whether the medicinal fluid currently being infused is one for which a stored protocol is not available. If the protocol required to infuse the current medicinal fluid is already stored in RAM 37 as a speed protocol, the logic proceeds to a block 104 wherein the required speed protocol is recalled from memory. However, if the protocol required for infusing the current medicinal fluid is not available among the three protocols that are stored, the logic proceeds to a block 106, which requires that the operator enter the protocol parameters one at a time as explained above in connection with FIG. 3.

After either a stored speed protocol is recalled from memory, or a new protocol is entered, the logic proceeds at a block 108, enabling the operator to review the protocol on display 18. Thereafter, a block 110 provides for initializing the pump for delivery of the fluid in accordance with the protocol, as indicated in a block 112. At any time, the operator may determine that a different protocol is required, as indicated in a decision block 114. Once the current protocol is completed, the operator may optionally repeat the protocol in accord with a block 116, entering the logic stream at block 110, or indicate that a different protocol is required, leading back to decision block 102.

It should also be noted that the current protocol can be assigned to a speed protocol at any time after the protocol is manually entered, i.e., after block 106. Once assigned to a speed protocol, the protocol can be reviewed without affecting the current operation of the pump under control of a different protocol. Due to design limitations, only three speed protocols are stored at one time in the preferred embodiment. Accordingly, if the current protocol is assigned to a speed protocol, it will replace one of three existing speed protocols stored in memory. If less than three speed protocols are stored, the current protocol can be stored as an additional speed protocol without replacing any other stored speed protocol.

Figure 5:
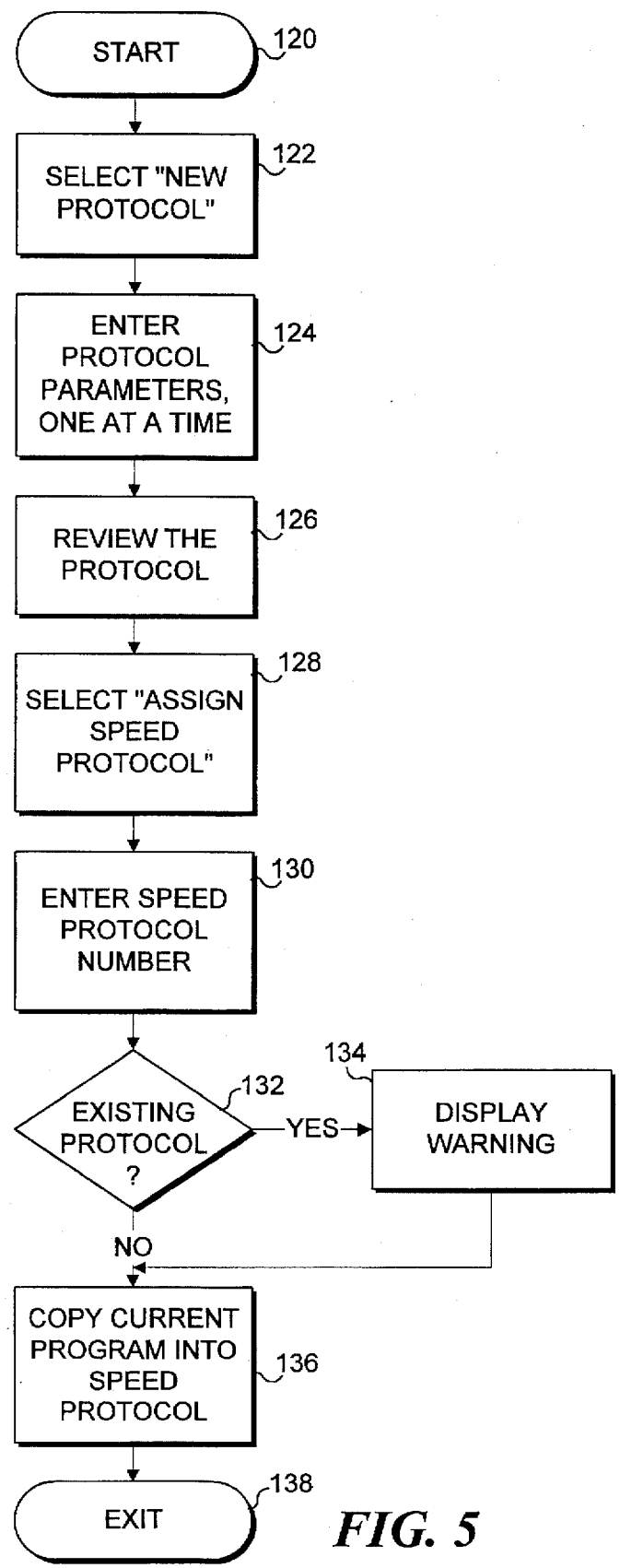
FIG. 5 is a flow chart showing the logical steps for assigning a new speed protocol.

The steps involved in assigning the parameters entered as a current protocol to a speed protocol are illustrated in FIG. 5, beginning at a start block 120. In a block 122, the operator again indicates that a new protocol is to be entered. Thereafter, as provided in a block 124, the operator is prompted to select the type of infusion and to enter the protocol parameters one at a time. Once the parameters have been entered, they are presented on display 18, enabling the operator to review the protocol as indicated in a block 126. The operator may change any of the parameters comprising the protocol, using the BACKUP key to return to the input screen. Display 18 can show three parameter lines at one time. A fourth line displays a prompt message to the operator, guiding the operator to carry out each of the steps necessary to review the protocol parameters.

In a block 128, the operator assigns the current protocol just reviewed in block 126 to a selected speed protocol. To designate the speed protocol to which the current parameters are to be assigned, the operator presses the OPTIONS key, selects "SPEED PROTOCOL" from the menu on the display, selects "RECALL," and enters a speed protocol number (1 through 3), as indicated in a block 130. The control then determines if the number entered by the operator is already assigned to an existing speed protocol in a decision block 132. If so, the control causes the display to present a warning to the operator in a block 134, noting that the selected number is assigned to an existing speed protocol. At this point, the operator can cancel the assignment of the speed protocol parameters to the selected number, enabling the previous speed protocol to be retained. However, if the operator elects to proceed with the replacement of the previous speed protocol that was assigned to the selected number, or if an existing speed protocol was not previously assigned to the number selected by the operator, the logic proceeds to a block 136. In block 136, the current program parameters are copied into memory, linked to the speed protocol number selected by the operator. The logic then exits at a block 138.

Figure 6:
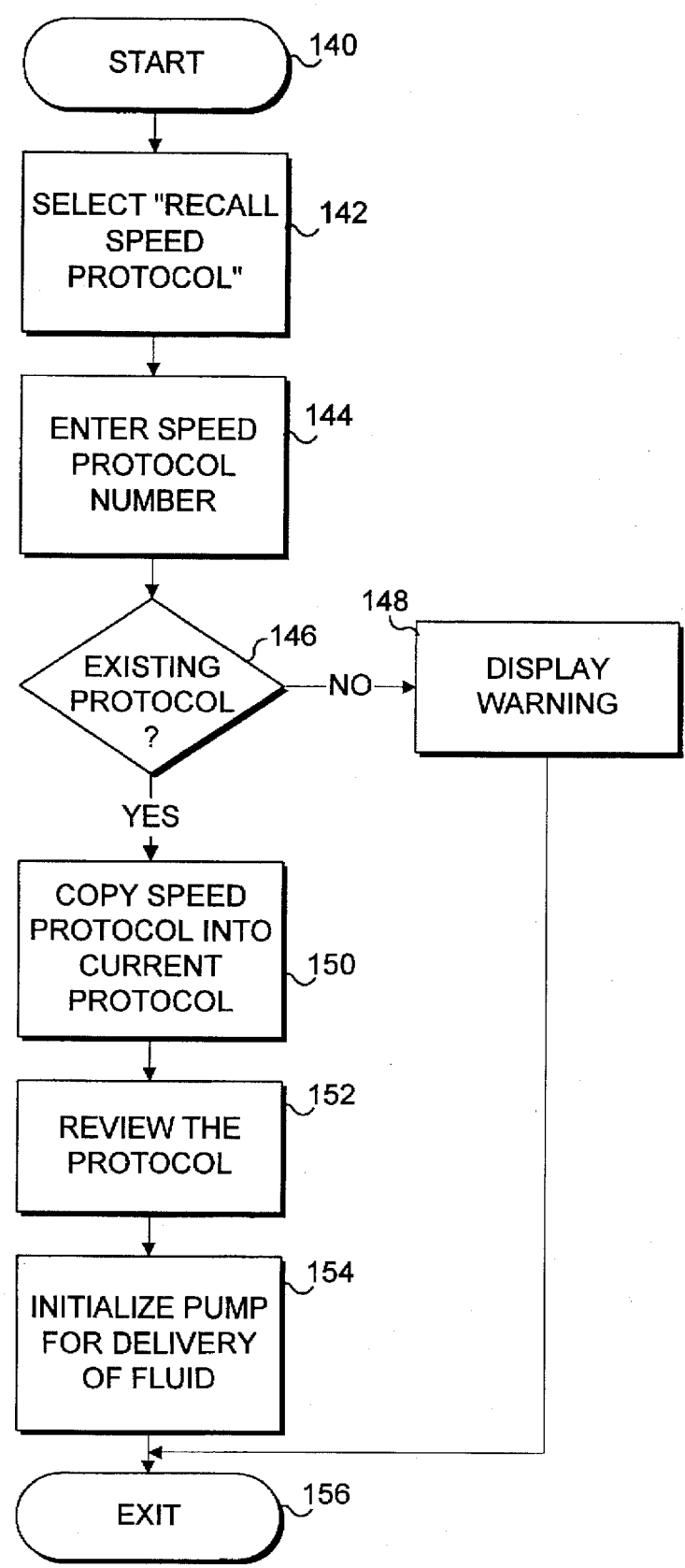
FIG. 6 is a flow chart showing the logical steps for recalling a speed protocol that is stored in memory.

If the operator determines that a medicinal fluid is to be infused into a patient for which a previously stored speed protocol can be used, the steps involved in recalling the speed protocol for use are implemented, as shown in FIG. 6. From a start block 140, the logic proceeds to a block 142 in which the operator selects a menu (displayed after the OPTIONS key is depressed and "SPEED PROTOCOL" is selected), which reads "RECALL." Assuming that the operator has selected this option, the control prompts the operator to enter a speed protocol number, as indicated in a block 144. A decision block 146 then determines if the speed protocol number entered by the operator in accordance with the logic of block 144 corresponds to that of an existing speed protocol. If the response to decision block 146 is negative, the control displays a warning to the operator indicating that the selected speed protocol number does not correspond to one stored in memory, as noted in a block 148. The logic then proceeds to exit, as provided in a block 156.

An affirmative response to decision block 146 leads to a block 150, wherein the selected speed protocol is copied into the current protocol for use in administering the medicinal fluid to the patient. At that point, the control causes the parameters of the now current protocol to be displayed to the operator for review, as indicated in a block 152. It should be noted that a speed protocol must be reviewed before it is implemented as the current controlling protocol to insure that the operator does not inadvertently apply an inappropriate protocol to administer a specific medicinal fluid. After the review is completed, in a block 154, the control initializes the pump for delivery of the medicinal fluid in accordance with the parameters of the now current speed protocol, which was just recalled from RAM 37. The procedure then exits in block 156.

Figure 7:
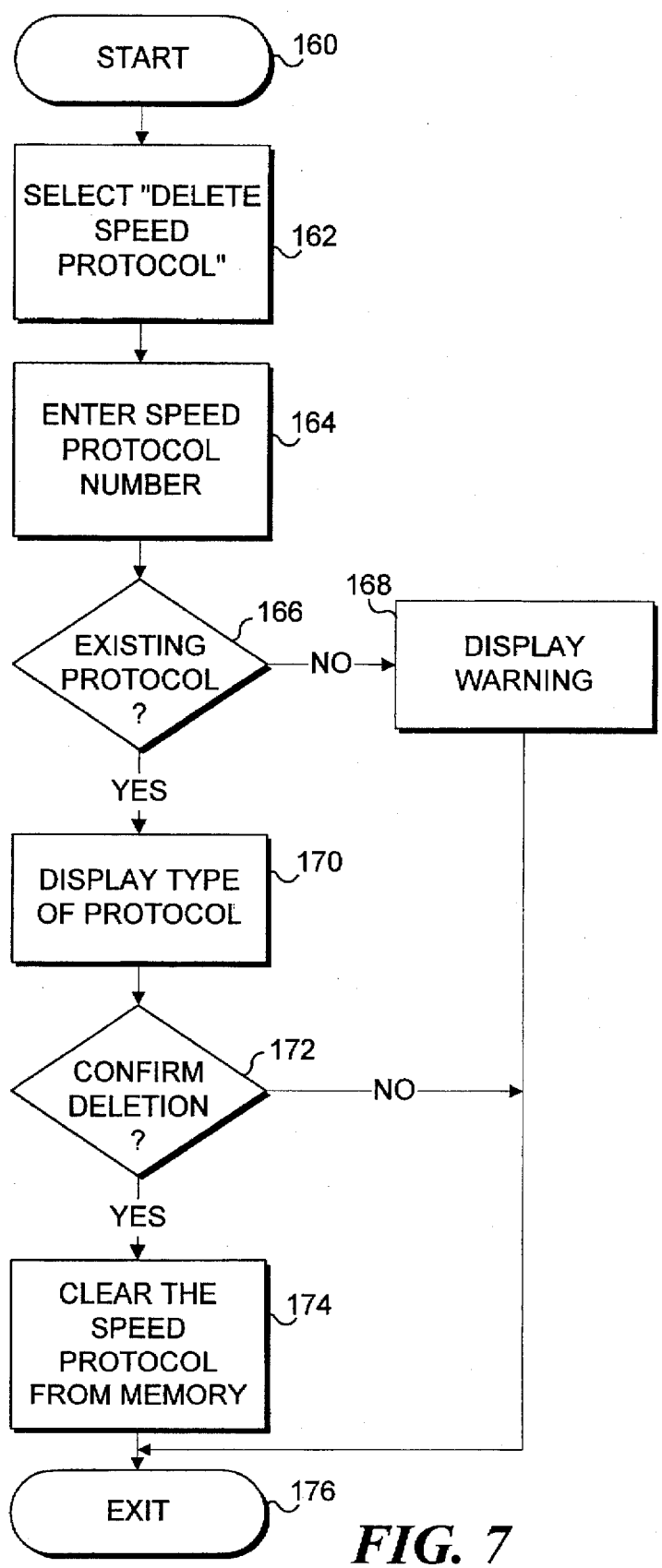
FIG. 7 is a flow chart illustrating the steps for deleting a speed protocol from among those stored in memory.

At times, an operator may wish to delete a speed protocol that is stored in memory. The steps required to carry out the deletion are illustrated in FIG. 7, beginning with a start block 160. In a block 162, the operator presses the OPTIONS key, selects "SPEED PROTOCOL", and selects an option labeled "DELETE" from the menu in display 18. In a block 164, the operator is prompted to enter the speed protocol number that is to be deleted. The control then determines whether the number entered by the operator corresponds to a stored speed protocol in a decision block 166. If not, a block 168 provides for displaying a warning to the operator, indicating that the operator has selected a non-valid speed protocol number for deletion. Thereafter, the logic proceeds to a block 176, where it exits from this procedure.

Assuming that the operator has entered a valid speed protocol number for deletion, the logic proceeds from decision block 166 to a block 170, which displays the type of protocol or infusion corresponding to the speed protocol number entered by the operator. The operator is then presented with the option of confirming the deletion (within the menu of display 18). If the operator declines to confirm the deletion of the selected speed protocol, the logic exits at block 176. However, if the operator confirms that the selected speed protocol should be deleted, the logic proceeds to a block 174, wherein the speed protocol is cleared from memory in RAM 37 by the control. Thereafter, the procedure concludes at block 176.

Figure 8:
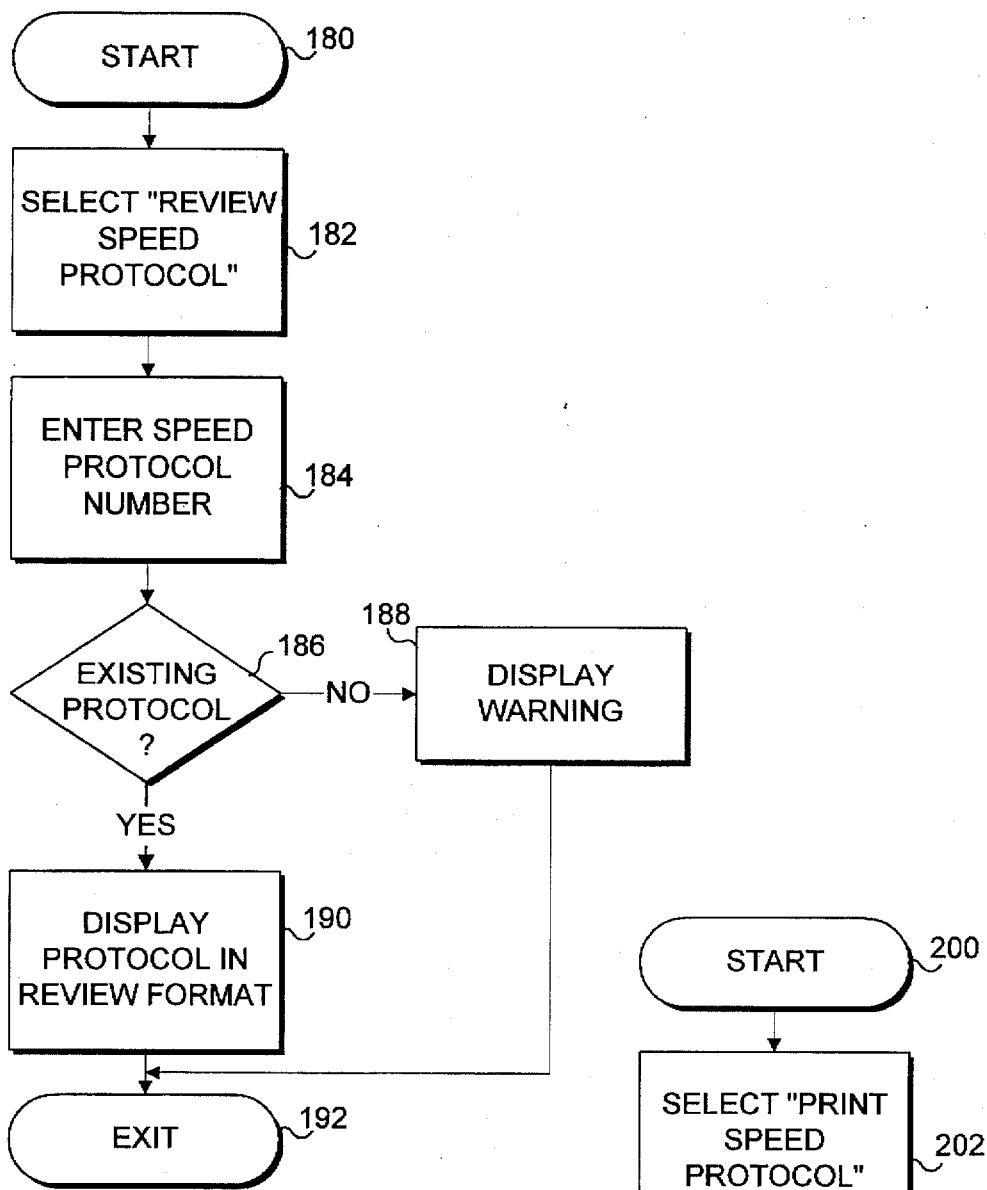
FIG. 8 is a flow chart showing the steps involved in reviewing a speed protocol.
Figure 9:
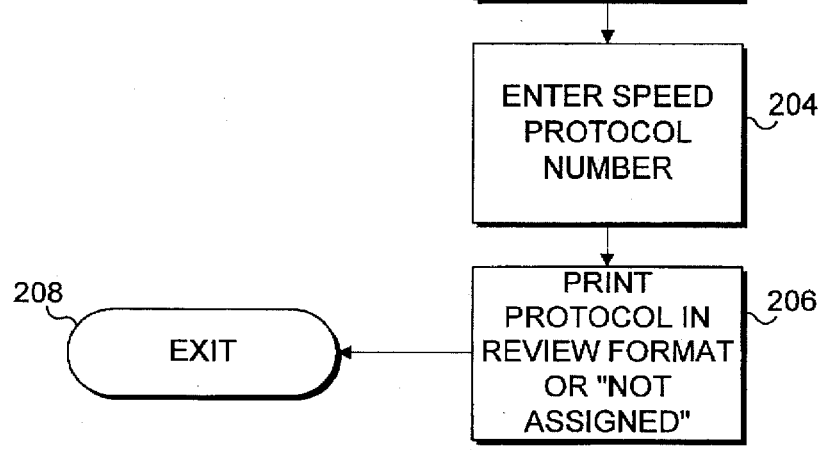
FIG. 9 is a flow chart showing the steps involved in printing a speed protocol.

Since the operator may not be familiar with each of the speed protocols stored in memory, provision is made for reviewing a selected speed protocol. This procedure, which can be elected at anytime without any effect on the current protocol being implemented to control the pump, is shown in FIG. 8, beginning with a start block 180. In a block 182, the operator is presented with an option in the menu displayed that reads "REVIEW." Once this option is selected, the logic proceeds to a block 184 in which the operator is prompted to enter the speed protocol number for the speed protocol that is to be reviewed. The control then determines if the number entered by the operator corresponds to a stored speed protocol in a decision block 186. If not, the control displays a warning to the operator in a block 188, indicating that an invalid speed protocol number has been entered and then proceeds to a block 192, to exit the procedure.

Assuming that the operator has entered a valid speed protocol number, a block 190 provides for displaying the selected speed protocol in the review format within display 18. This review format identifies the type of the speed protocol (i.e., the type of infusion) and any other parameters specific to that speed protocol. Once the operator has concluded reviewing the selected speed protocol, the logic exits in block 192.

Finally, the operator can selectively print a copy of any of the speed protocols through a serial data link (not shown) on pump 50. Beginning at a start block 200, the operator is presented with a menu option labeled "PRINT," as indicated in a block 202. Thereafter, the operator is prompted to enter the speed protocol number that is to be printed, as indicated in a block 204. Once the speed protocol number is entered, the control transmits the data in the review format to an external printer (or to a computer coupled to a printer) through an RS-232 port, which is disposed on the bottom of the pump. In the event that the operator has selected a speed protocol number that is not assigned to any speed protocol stored in memory, the control prints the notation "NOT ASSIGNED." Following the logic in block 206, the procedure exits, as provided in a block 208.

As will be evident from the foregoing disclosure, the use of stored speed protocols enables the operator to selectively infuse any medicinal fluid for which a stored speed protocol is appropriate without the need to reenter the parameters that control the pump during the infusion process. As a result, the likelihood of errors that might be introduced when reentering the parameters is decreased. More importantly, the operator is saved the trouble and time required to reenter parameters necessary to define protocols that are consistently used for infusing medicinal fluids, if the required protocol is among those stored in memory. By providing additional memory, the preferred embodiment disclosed above can readily be modified to enable more than three speed protocols to be stored.

Although the present invention has been described in connection with the preferred form of practicing it, it will be understood by those of ordinary skill in the art that many modifications can be made thereto within the scope of the claims that follow. Accordingly, it is not intended that the scope of the invention in any way be limited by the above description, but that it be determined entirely by reference to the claims that follow.

The invention in which an exclusive right is claimed is defined by the following:

1. A pump for administering a fluid to a patient, comprising:
   (a) a fluid drive unit that is adapted to couple with a fluid line and to force fluid from a source to the patient through the fluid line;
   (b) a control that is coupled to the fluid drive unit to contol its operation;
   (c) a memory in which a plurality of protocols are stored, said protocols each specifying at least one parameter used to control the fluid drive; and
   (d) a user interface that is integral with the pump and is coupled to the control and to the memory to enable the operator to enter said at least one parameter for any of said plurality of protocols, store said protocol with said at least one parameter included so that said at least one parameter is already set when said protocol is next selected, and to select one of said plurality of protocols to be the current protocol for use by the control in actively controlling the operation of the drive unit so as to administer the fluid to the patient in accordance with said protocol that is selected.

2. The pump of claim 1, wherein the parameter comprises one of a continuous fluid flow, an intermittent fluid flow, and a bolus fluid flow.

3. The pump of claim 1, wherein the parameter comprises one of a rate of fluid flow, a volume of fluid flow, a time of fluid flow, and a duration of fluid flow.

4. The pump of claim 1, wherein the user interface enables the operator to define a current protocol and to store the current protocol as one of the plurality of protocols in the memory.

5. The pump of claim 1, wherein the control cooperates with the user interface to enable the operator to review one of the plurality of protocols stored in the memory while the drive unit is being operated in accordance with a different one of the plurality of protocols.

6. The pump of claim 1, wherein said at least one parameter comprises a varying rate of fluid flow.

7. The pump of claim 1, wherein the user interface enables the operator to recall one of the plurality of protocols from memory as a currently active protocol used by the control in controlling the drive unit, and enables the operator to modify said currently active protocol prior to storing it in the memory.

8. A pump for administering at least one medicinal fluid to a patient through a fluid line, said pump comprising:

(a) a microprocessor controller responsive to program steps stored in a memory associated with the microprocessor controller, said program steps effecting control of the pump in accordance with an operator selected protocol;

(b) a fluid pumping unit for forcing fluid into the patient through the fluid line, said fluid pumping unit being electrically coupled to the microprocessor controller and controlled thereby; and (c) a control panel that is electrically coupled to the microprocessor controller, integral with the pump, said control panel including a display and a plurality of switches that enable an operator to enter parameters for each of a plurality of protocols that are stored in the memory, said parameters entered for each protocol being stored and appearing on the display when a protocol is next selected, said switches also enabling the operator to recall one of the plurality of protocols as a current protocol for controling the fluid pumping unit.

9. The pump of claim 8, wherein the microprocessor controller enables the operator to review parameters for one of the stored protocols while using a different protocol to control the fluid pumping unit.

10. The pump of claim 8, wherein the parameters that define the plurality of protocols comprise at least one of a fluid flow rate, a fluid volume, a duration for fluid flow through the pump, and a time to initiate fluid flow through the pump.

11. The pump of claim 8, wherein the plurality of protocols comprise at least one of a parenteral nutrition fluid delivery protocol, a pain management fluid delivery protocol, an intermittent fluid delivery protocol, a variable time fluid delivery protocol, and a continuous fluid delivery protocol.

12. The pump of claim 11, wherein the parenteral nutrition fluid delivery protocol comprises an operator selected parameter for at least one of a continuous fluid flow, and a continuous fluid flow with a tapering fluid flow rate.

13. The pump of claim 11, wherein the pain management fluid delivery protocol comprises an operator selected parameter for at least one of an intravenous fluid administration, an epidural fluid administration, and a subcutaneous fluid administration.

14. The pump of claim 11, wherein the variable time fluid protocol comprises an operator selected parameter for at least one dose designating at least one of a percentage of volume, a rate of flow, and a volume.

15. The pump of claim 8, wherein the program steps enable the operator to print a selected protocol while the pump is administering the fluid in accordance with a different protocol.

16. The pump of claim 8, wherein the parameters selected to define the plurality of protocols include a keep vein open fluid flow rate option.

17. The pump of claim 8, wherein the parameters selected to define the plurality of protocols include a bolus injection option.

18. The pump of claim 8, wherein the program steps enable the operator to recall one of the plurality of protocols as a current protocol and to modify said current protocol by changing at least one of the parameters that define it.

19. The pump of claim 8, wherein the program steps provide prompts to the operator on the display that indicate the parameters that are selectable by the operator.

20. The pump of claim 19, wherein the prompts indicate a plurality of units of measurement to enable the operator to select the units of measurement for at least one of the parameters that define the plurality of protocols stored in the memory.

21. The pump of claim 8, wherein the program steps require that any of the plurality of protocols recalled from memory be reviewed by the operator before the fluid pumping unit is controlled with said protocol.

22. The pump of claim 8, further comprising a backup battery power supply to maintain storage of the plurality of protocols in the memory when the pump is disconnected from another source of power.

* * * * *